United States Patent
Jasra et al.

(10) Patent No.: US 6,730,814 B1
(45) Date of Patent: May 4, 2004

(54) CLAY BASED CATALYTIC PROCESS FOR THE PREPARATION OF ACYLATED AROMATIC ETHERS

(75) Inventors: Rakesh Vir Jasra, Gujarat (IN); Muthusamy Sengodagounder, Gujarat (IN); Yogiraj Mansukhlal Badheka, Gujarat (IN)

(73) Assignee: Council of Scientific and Industrial Research, New Delhi, IN (US)

( * ) Notice: Subject to any disclaimer, the term of this patent is extended or adjusted under 35 U.S.C. 154(b) by 0 days.

(21) Appl. No.: 10/341,606

(22) Filed: Jan. 14, 2003

(51) Int. Cl.[7] .......................... C07C 45/46; C07C 49/76
(52) U.S. Cl. ...................... 568/322; 568/323; 568/331; 568/336
(58) Field of Search ................................ 568/322, 323, 568/331, 336

(56) References Cited

U.S. PATENT DOCUMENTS 5,637,773 A * 6/1997 Desmurs et al. ............ 568/319
5,817,878 A * 10/1998 Spagnol et al. ............. 568/319
6,274,741 B1 * 8/2001 Choudary et al. .......... 548/540

OTHER PUBLICATIONS

Kawada et al. Friedel–Crafts Reactions Catalyzed by Rare Earth Metal Triflouromethanesulfonates.□□Bull. Chem. Soc. Jpn., 73, p 2325–2333 (2000).*

* cited by examiner

Primary Examiner—Johann Richter
Assistant Examiner—SiKarl A. Witherspoon
(74) Attorney, Agent, or Firm—Nixon & Vanderhye P.C.

(57) ABSTRACT

This invention relates to a process for the preparation of acylated aromatic ethers, in particular the acylation of anisole (methoxybenzene) and veratrole (1,2-dimethoxybenzene) for the preparation of corresponding acylated aromatic ether, namely, p-methoxyacetophenone and 3,4-dimethoxyacetophenone respectively, using clay based heterogeneous catalysts, and their lanthanide exchanged forms at moderate temperature and pressure with high selectivity.

16 Claims, No Drawings

US 6,730,814 B1

CLAY BASED CATALYTIC PROCESS FOR THE PREPARATION OF ACYLATED AROMATIC ETHERS

FIELD OF THE INVENTION

The present invention relates to a clay based catalytic process for the preparation of acylated aromatic ethers. More particularly, the present invention relates to the catalyzed acylation of anisole (methoxybenzene) and veratrole (1,2-dimethoxybenzene) for the preparation of acylated aromatic ether, namely, p-methoxyacetophenone and 3,4-dimethoxyacetophenone respectively, using a series of lantanide cation exchanged clay based catalysts.

BACKGROUND OF THE INVENTION

Acylated aromatic ethers are of commercial importance in fine chemicals industries, as many synthetic fragrances and pharmaceuticals contains an acyl group, and these ethers are useful intermediates. Acylated anisole is used for synthesis of 2-(4-Methoxybenzoyl) benzoic acid, the sodium salt of which is used as sweetening agent. Similarly, acylated veratrole is a synthon for preparation of vesnarinone 1-(3, 4-Dimethoxybenzoyl)-4(1,2,3,4-tetrahydro-2-oxo-6-quinolinyl) piperazine which is a cardiotonic drug.

Reference is made to U.S. Pat. No. 62747441 B1 (Aug. 14, 2001, B. M. Choudary et al.) wherein it is disclosed that acylation of heteroaromtic compounds like furan, thiophene, or pyrrole with the anhydride of $C_{2-5}$ carboxylic acid (e.g. acetic anhydride) was carried out using $Fe^{+3}$ exchanged Montmorillonite clay. The reaction was carried out in the temperature range of 0 to 130° C. for 1 to 24 hours and the 2-acylaromatic compound was separated by conventional methods to obtain 2-acetylpyrrole of high purity. The drawback of this process is the longer reaction time and high temperature.

Reference is made to the work of B. M. Choudary et al, Applied Catalysis A, General 171 (1998) 155–160 which describes the acylation of aromatic ethers with acid anhydrides in the presence of cation exchanged clays viz., $Fe^{+3}$ and $Zn^{+2}$ exchanged montmorillonite clays. The reaction mixture of 46 millimoles of anisole and 10 millimoles of acetic anhydride and 250 mg of catalysts was stirred under nitrogen atmosphere. After 10 hours it gives conversion in the range of 25 to 70 percent. The drawback of this process is long reaction time, and the catalyst shows loss in activity. Reference is made to U.S. Pat. No. 5,637,773 (1993: Jean-Roger Desmurs et al.) wherein it is disclosed that 40 millimoles of an aromatic substrates and 10 millimoles of acylating agents with excess amount of Bismuth halide as a catalyst, was mixed at room temperature and then refluxed the reaction mixture for 6 hours to gives 67% of 4-acylated anisole. The drawback of this process is that more than stochiometric amounts of bismuth chloride was used and also poses problem of post-reaction catalysts separation. Furthermore, the Lewis acid must be eliminated from the reaction medium by carrying out acidic or basic hydrolysis at the end of the reaction.

Reference is made to German Patent DE 3809260 (1989, Botta A., et al.) wherein anisole and acetic anhydride were stirred for 3 hours with Mordenite zeolite catalysts at 160° C. under 20 bar of nitrogen pressure to give 75% conversion with 98% selectivity for p-methoxyacetophenone. This process has disadvantage of operating at high temperature and very high pressure and also needs a solvent for uniform mixing. Reference is made to Japanese Patent 1993-317557 (19931217. C. A.124;8397 Myata, Akira et al.) wherein a mixture of veratrole and propionyl chloride, in the presence of Zeolite-β was refluxed for three hours to give ca, 70% of 3,4-dimethoxypropiophenone. The drawback of the process is that it uses propionyl chloride as an acylating agent, which generates toxic hydrochloric acid during acylation reaction Reference is made to the work of C. Kuroda et al, (Sei. Papers Inst. Phys. Chem. Res. 18, pp 51–60 (1932)) which describes the preparation of methoxyacetophenones by the reaction of an aromatic compound carrying methoxy group with acetyl chloride in the presence of excess amount of $AlCl_3$ to obtain high conversions. This process has disadvantages like more than stochiometric amounts of aluminum chloride due to complexation with the ketone formed and also involved process of post reaction effluent treatment and use of corrosive and irritant $AlCl_3$. The major drawback of the above stated process is separation of catalysts after completion of the reaction. This necessitates a long, expensive treatment following hydrolysis, extraction of the organic phase, separation of organic and aqueous phase and even drying of latter. Further, there are problems with aqueous saline effluent which has to be neutralized and which necessities additional operation. The Lewis acid cannot be recycled, as it has been hydrolyzed.

Reference is made to the work of H. Burton and P. F. G. Praill (Journal of Chemical Society, April-1950, pp-1203–1206) wherein it is reported that Acetyl perchlorate formed in-situ from silver perchlorates and acetyl chloride, is an effective acylating agent and will convert anisole into p-methoxyacetophenone in about 70% yield. However, this process has disadvantages of using perchlorates which is hazardous chemical. Reference is made to the work of E. J, Bourne, et al. (Journal of Chemical Society, March-1951, pp-718–720) wherein trifluoroacetic anhydride catalyst is shown to promote, the condensation between suitably activated aromatic compound and carboxylic acid or sulphonic acid to give ketones or sulphones, respectively. In this process, reaction was done at room temperature. Anisole was added to a mixture of trifluroacetic anhydride and acetic acid. After three hours the solution was poured into the excess of sodium hydrogen carbonate solution and then extracted by chloroform The extract were dried, filtered and evaporated to dry syrup. After crystallization it gave 78% of p-methoxyacetophenone.

The reported process is multi-step process wherein separation of the product with very high recovery is a limitation.

Reference is made to the work of Cullinane N. M. et al. (Journal of Chemical Society, Feb-952, pp-376–380) wherein acylation of benzene, toluene and anisole is reported using $TiCl_4$ as a catalyst. Acids, acid chlorides and anhydrides were used as the acylating agents. Acid is reported to be the least and anhydride the most effective towards the formation of acylated products. With anisole (0.15 g-mols) and acetic anhydride (0.1 g-mol) and titanium tetrachloride (0.22 g-mol), the yield of p-acylated product was reported 76% after 4 hours. With anisole (0.2 g-mols) and benzoic acid (0.2 g-mols) and titanium tetrachloride (0.4 g-mols) the yield of p-acylated product was 63% after 1.5 hours. The process has disadvantage of separation of product, as it requires more than one step, like hydrolysis, separation of organic layer and finally removal of solvent at reduced pressure.

OBJECTS OF THE INVENTION

The main object of the present invention is to provide clay based catalytic process for the preparation of acylated aromatic ethers, which obviates the drawbacks as detailed above.

Another object of the invention is to develop clay based acylation process for aromatic ethers, which operates at moderate conditions of pressure, temperature and without the requirement of any solvent and yields high conversions for veratrole and for anisole.

Another object of the invention is to provide a process using solid acid heterogeneous catalysts, which are environmentally friendly, safe in handling and the acylating agent does not generate any hazardous byproduct.

Another object of the invention is to provide a process wherein acylation of aromatic ether occurs selectively at para position.

Another object of the invention is to provide a process where acylation of aromatic ether is carried out catalytically with high atom efficiency without giving rise to byproducts.

SUMMARY OF THE INVENTION

Accordingly the present invention provides a process for the preparation of an acylated aromatic ether which comprises acylating the aromatic ether with an acylating agent in presence of a solid acid heterogeneous catalyst comprising a rare earth cation exchanged clay based catalyst, separating the catalyst and the acylated aromatic ether obtained.

In one embodiment of the invention, the lanthanide cation exchanged clay catalyst is an upgraded smectite clay wherein the hydrogen ion is exchanged with a sodium ion.

In another embodiment of the invention, the hydrogen ion is exchanged with a sodium ion using an acid selected from the group consisting of HCl, $HNO_3$, and an organic acid.

In another embodiment of the invention, the rare earth ion is selected from the group consisting of lanthanum, cerium, neodymium, praseodymium and samarium.

In a further embodiment of the invention, the amount of rare earth ion in the catalyst is in the range of 5 to 10 weight % of the clay.

In a further embodiment of the invention, the rare earth ion is obtained using a soluble salt of the rare earth selected from the group consisting of nitrate, chloride and acetate.

In another embodiment of the invention, the acylation of the aromatic ether is carried out in a single step under solvent free condition and at a temperature in the range of 80 to 120° C. and under atmospheric conditions without generating any by-product.

In a further embodiment of the invention, the acylation of the aromatic ether is carried out at a temperature of 100° C.

In another embodiment of the invention, the acylating agent is selected from the group consisting of a chloride and a carboxylic acid anhydride.

In another embodiment of the invention, the carboxylic acid anhydride is acetic acid anhydride or a homologue thereof.

In another embodiment of the invention, the catalyst is separated and recycled.

In another embodiment of the invention, the aromatic ether is selected from the group consisting of veratrole and anisole.

In another embodiment of the invention the process is solvent free with the aromatic ether itself acting as the solvent.

In yet another embodiment of the invention the catalytic reaction is carried Out in the range from 1 to 20 atmospheres.

In yet another embodiment of the present invention the ether to catalyst ratio is in the range of 1.3 to 1:5.

The invention also relates to a clay based catalytic process for the preparation of an acylated aromatic ether which comprises (i) preparing upgraded smectite clay in the range of 0.5 to 5% weight percent; (ii) drying the clay in the temperature of 80 to 120° C. for 8 to 12 hours; (iii) exchanging hydrogen ion for sodium ion using a mineral acid selected from the group consisting of HCl and HNO3 or an organic acid; (iv) preparing Lanthanide exchanged clay using a soluble salt of a lanthanide cation; (v) maintaining the ether to catalyst ratio in the range of 1 to 5; mixing the catalyst so prepared with the aromatic ether and an acylating agent and acylating the aromatic ether at a reaction temperature in the range of 80 to 120° C. and time in the range of 1 to 9 hours under solvent free reaction mixture at atmospheric pressure; (vi) separating the catalyst and the acylated product by distillation.

DETAILED DESCRIPTION OF THE INVENTION

In a typical procedure for the preparation of a clay based catalysts, the raw clay is upgraded by sedimentation to remove quartz, grits etc impurities. Wet solid clay is separated from the clay slurry by ultracentrifuge and naturally dried from 6 to 12 hours, followed by drying at 80° C. to 120° C. for 4 to 8 hours. Thus dried clay was treated with acid solution to convert the clay into H-form 10 gm of the clay thus prepared H-form of clay was refluxed with 100 ml of 0.01 M solution of soluble salt like nitrate, chloride or acetate of relative lanthanide cations for 6 hours. Then catalysts was filtered washed with hot distilled water till the filtrate became anion free and dried overnight 110° C. for removing the moistures, clay was activated at 120° C. for 4–6 hrs before using for reactions. A typical chemical analysis of clay used for making catalysts was.

| SiO2 | $Al_2O_3$ | $R_2O_3$ | $Na_2O$ | $K_2O$ | MgO | CaO | LOI |
|---|---|---|---|---|---|---|---|
| 52.61% | 7.08% | 31.43% | 0.09% | 0.33% | 2.46% | 3.66% | 6.14% |

The clays prepared were characterized for crystallinity by using X-ray powder diffraction using Philips X'perts MPD model and for BET surface area using Micromeritics ASAP-surface area analyzers.

Catalytic studies using above catalysts were done in continuous stirred tank reactor (CSTR) of 50 ml capacity having temperature controller, water circulator, magnetic stirrer and moisture trap. Typically, 5.5 g of veratrole (or 4.3 g of anisole) and 3.5 g of acetic anhydride were taken in a 50 ml capacity round bottom flask to which 2 gm of the catalyst after activation at 120° C. for 4 to 10 hours in muffle furnace was added. The round bottom flask was fitted with a condenser through which constant temperature water was circulated. Moisture trap was attached at the end of the condenser. The contents of the flask were constantly stirred using a magnetic stirrer. The flask was kept in an oil bath whose temperature was slowly raised to desired reaction temperature. The contents of the flask were analyzed by gas chromatography at different time intervals ranging from 1 to 8 hours. The yield was followed over time by taking aliquots which were analyzed by Gas Chromatography HP model 6890 using capillary column HP-5. Percent yield of p-acyl anisole or p-acyl veratrole was calculated using following equation Percent Yield=number of moles of para acyl aromatic ether actually formed/number of moles of para acyl aromatic ether theoretically expected, In the present invention upgraded clay was exchanged with soluble salt of lanthanide cations like lanthanum cerium, neodymium, praseodymium, samarium ranging from 5 to 10 wt % of the clay to make them more active towards acylation of anisole and veratrole. Further this improved catalytic process obviates the need of any solvent and the reaction can be carried out at atmospheric pressure. The lanthanide cations in the interlayer space of clays helps the catalytic conversion to be carried out at moderate temperature.

The inventive steps adopted in this invention are: (i) Clays are modified with rare earth in the range of 5 to 10 weight % to make the catalysts more compatible with acylation reactions; (ii) the acylation reaction is carried out in single step so that the multi-step process can be avoided; (iii) the lower temperature and pressure favors the selectivity for para position, which is desired; (iv) the catalytic reaction proceeds at relatively moderate temperature of 100° C. and at atmospheric pressure, which obviates the need of high temperature and pressure, (v) acylation occurs without use of any solvent and without using hazardous and effluent generating acylating agent.

The following examples are given by way of illustration and therefore should not be construed to limit the scope of the present invention.

EXAMPLE 1

100 grams of raw clay was mixed with 10 liters of distilled water and thus formed slurry was thoroughly stirred at ambient temperature for 6 hours. The slurry was then sedimented for 24 hours followed by decantation of suspended clay solution. Upgraded solid clay was recovered first by natural drying followed by drying in oven at 110° C. for 6 hours. Thus crude clay was further refluxed with 2 normal solution of sulfuric acid in a round bottom flask with a solid to liquid ratio 1;5 at 80° C. for 2 hours. Clay was filtered and washed with distilled water till it became free from sulphate ion as tested by barium sulphate and was finally dried at 110° C. for 6 hours. Thus obtained clay was termed as H-clay. 40 milimoles of aromatic ether and 40 milimoles of acetic anhydride were reacted with 2 gms of H-Clay catalysts in abut 50 ml capacity of round bottom flask kept in oil bath and the temperature of oil bath was slowly raised to desired temperature of 100° C. The round bottom flask provided with a water-circulator, temperature-controller, magnetic stirrer and moisture trap The contents of the flask were analyzed by gas chromatography at different time intervals ranging from 1 to 9 hours. The percent yield of p-acyl veratrole and p-acyl anisole respectively shown in table 1a and 1b from 31 to 77% and 12 to 41% were obtained.

EXAMPLE 2

10 grams of H-clay prepared as described in Example-1 was refluxed with 100 ml of the 0.01 M solution of soluble salt (nitrate, chloride or acetate) of Lanthanum for 6 hours. Then the catalysts was filtered, washed with hot distilled water till the filtrated became anion free and dried overnight at 110° C. for removing the moisture Clay catalysts, La-clay thus obtained was activated at 120° C. for 4 to 6 hours before using for reaction. 40 milimoles of aromatic ether and 40 milimoles of acetic anhydride were reacted with 2 grams catalyst in abut 50 ml capacity of round bottom flask kept in oil bath and the temperature of oil bath was slowly raised to desired temperature of 100° C. The round bottom flask provided with a water-circulator, temperature-controller, magnetic stirrer and moisture trap. The contents of the flask were analyzed by gas chromatography at different time intervals ranging from 1 to 5 hours. The percent yield of p-acyl veratrole and p-acyl anisole respectively shown in table 1a and 1b form 56 to 88% and 38 to 49% were obtained.

EXAMPLE 3

10 grams of H-clay prepared as described in Example-1 was refluxed with 100 ml of the 0.01 M solution of soluble salt (nitrate, chloride or acetate) of cerium for 6 hours. Then the catalysts was filtered, washed with hot distilled water till the filtrated became anion free and dried overnight at 110° C. for removing the moisture. Clay catalysts, Ce-clay thus obtained was activated at 120° C. for 4 to 6 hours before using for reaction. 40 milimoles of aromatic ether and 40 milimoles of acetic anhydride were reacted with 2 grams catalysts in abut 50 ml capacity of round bottom flask kept in oil bath and the temperature of oil bath was slowly raised to desired temperature of 100° C. The round bottom flask provided with a water-circulator, temperature-controller, magnetic stirrer and moisture trap. The contents of the flask were analyzed by gas chromatography at different time intervals ranging from 1 to 5 hours. The percent yield of p-acyl veratrole and p-acyl anisole respectively shown in table 1a and 1b from 57 to 91% and 35 to 52% were obtained.

EXAMPLE 4

10 grams of H-clay prepared as described in Example-1 was refluxed with 100 ml of the 0.01 M solution of soluble salt (nitrate, chloride or acetate) of neodymium for 6 hours. Then the catalysts was filtered, washed with hot distilled water till the filtrated became anion free and dried overnight at 110° C. for removing the moisture. Clay catalysts, La-clay thus obtained was activated at 120° C. for 4 to 6 hours before using for reaction. 40 milimoles of aromatic ether and 40 milimoles of acetic anhydride were reacted with 2 grams catalysts in abut 50 ml capacity of round bottom flask kept in oil bath and the temperature of oil bath was slowly raised to desired temperature of 100° C. The round bottom flask provided with a water-circulator, temperature-controller, magnetic stirrer and moisture trap. The contents of the flask were analyzed by gas chromatography at different time intervals ranging from 1 to 5 hours. The percent yield of p-acyl veratrole and p-acyl anisole respectively shown in table 1a and 1b from 49 to 71% and 8 to 16% were obtained.

EXAMPLE 5

10 grams of H-clay prepared as described in Example-1 was refluxed with 100 ml of the 0.01 M solution of soluble salt (nitrate, chloride or acetate) of praseodymium for 6 hours. Then the catalysts was filtered, washed with hot distilled water till the filtrated became anion free and dried overnight at 110° C. for removing the moisture. Clay catalysts, Pr-clay thus obtained was activated at 120° C. for 4 to 6 hours before using for reaction. 40 milimoles of aromatic ether and 40 milimoles of acetic anhydride were reacted with 2 grams catalysts in abut 50 ml capacity of round bottom flask kept in oil bath and the temperature of oil bath was slowly raised to desired temperature of 100° C. The round bottom flask provided with a water-circulator, temperature-controller, magnetic stirrer and moisture trap. The contents of the flask were analyzed by gas chromatography at different time intervals ranging from 1 to 5 hours. The percent yield of p-acyl veratrole and p-acyl anisole respectively shown in table 1a and 1b from 23 to 62% and 12 to 39% were obtained.

EXAMPLE 6

10 grams of H-clay prepared as described in Example-1 was refluxed with 100 ml of the 0.01 M solution of soluble salt (nitrate, chloride or acetate) of samarium for 6 hours. Then the catalysts was filtered, washed with hot distilled water till the filtrated became anion free and dried overnight at 110° C. for removing the moisture. Clay catalysts, Sm-clay thus obtained was activated at 120° C. for 4 to 6 hours before using for reaction. 40 milimoles of aromatic ether and 40 milimoles of acetic anhydride were reacted with 2 grams catalysts in abut 50 ml capacity of round bottom flask kept in oil bath and the temperature of oil bath was slowly raised to desired temperature of 100° C. The round bottom flask provided with a water-circulator, temperature-controller, magnetic stirrer and moisture trap. The contents of the flask were analyzed by gas chromatography at different time intervals ranging from 1 to 4 hours. The percent yield of p-acyl veratrole and p-acyl anisole respectively shown in table 1a and 1b from 56 to 63% and 6 to 39% were obtained

EXAMPLE 7

Clay catalysts used in Example-3 was regenerated by washing with a polar solvent like acetone and heated at 120 for 4 hours and reused for acylation of veratrole as described in example-3. Percent yield of veratrole after first and second regeneration cycle were 80% and 75% respectively.

EXAMPLE 8

10 grams of H-clay prepared as described in Example-1 was refluxed with 100 ml of the 0.01 M solution of soluble salt like nitrate, chloride or acetate of lanthanum for 6 hours. Then the catalysts was filtered, washed with hot distilled water till the filtrated became anion free and dried overnight at 110° C. for removing the moisture. Clay catalysts, La-clay thus obtained was activated at 120 ° C. for 4 to 6 hours before using for reaction. 40 milimoles of aromatic ether and 40 milimoles of acetic anhydride were reacted with 2 grams catalysts in about 50 ml capacity of round bottom flask kept in oil bath and the temperature of oil bath was slowly raised to desired temperature of 80° C. The round bottom flask provided with a water-circulator, temperature-controller, magnetic stirrer and moisture trap. The contents of the flask were analyzed by gas chromatography at different time intervals ranging from 1 to 4 hours. The percent yield of p-acyl veratrole and p-acyl anisole respectively shown in table 1a and 1b from 29 to 40% and 15 to 30% were obtained.

product by the sum of the all substances produced in the stochiometric equation, i.e. if we consider the acylation of the anisole and veratrole by acetic anhydride by using clay, reactions are represented as under.

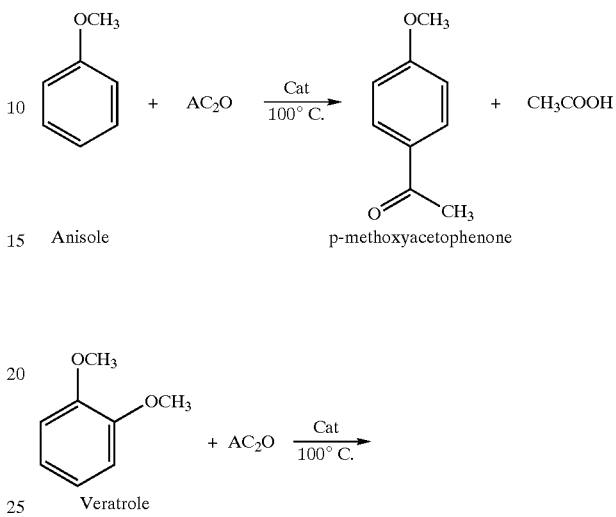

TABLE 1a

Percent yields of p-acyl veratrole obtained on acylation of veratrole using different catalysts.

| Ex. No. | Catalyst | Yield of 3,4-Dimethoxyacetophenone(%) | | | | | | | | |
|---|---|---|---|---|---|---|---|---|---|---|
| | | 1 hr | 2 hr | 3 hr | 4 hr | 5 hr | 6 hr | 7 hr | 8 hr | 9 hr |
| 1 | H-Clay | 31 | 59 | 52 | 58 | 65 | 69 | 72 | 77 | 69 |
| 2 | La-Clay | 56 | 68 | 86 | 88 | 78 | — | — | — | — |
| 3 | Ce-Clay | 57 | 69 | 75 | 91 | 85 | — | — | — | — |
| 4 | Nd-Clay | 49 | 52 | 59 | 71 | 68 | — | — | — | — |
| 5 | Pr-Clay | 23 | 42 | 55 | 62 | 58 | — | — | — | — |
| 6 | Sm-Clay | 56 | 57 | 63 | 59 | — | — | — | — | — |
| 8 | La-Clay | 29 | 33 | 38 | 40 | 37 | — | — | — | — |

TABLE 1b

Percent yields of p-acyl anisole obtained on acylation of anisole using different catalysts.

| Ex..No. | Catalysts | Yield of P-methoxyacetophenone(%) | | | | | | |
|---|---|---|---|---|---|---|---|---|
| | | 1 hr | 2 hr | 3 hr | 4 hr | 5 hr | 6 hr | 7 hr |
| 1 | H-Clay | 12 | 13 | 15 | 19 | 41 | 33 | 30 |
| 2 | La-Clay | 38 | 40 | 42 | 59 | 49 | — | — |
| 3 | Ce-Clay | 35 | 42 | 59 | 62 | 58 | — | — |
| 4 | Nd-Clay | 8 | 12 | 14 | 16 | 14 | — | — |
| 5 | Pr-Clay | 12 | 14 | 31 | 36 | 39 | 37 | — |
| 6 | Sm-Clay | 6 | 23 | 39 | 32 | — | — | — |
| 8 | La-Clay | 15 | 19 | 24 | 30 | 27 | — | — |

The mail advantages of the present invention are:
1. Acylation is done without use of any solvent, i.e., it is solvent free single step reaction.
2. High atom utilization and low mass ratio of waste to desired product (E-factor) for these conversion reflecting the environmentally friendly production of p-acylated aromatic ether. Atom utilization is calculated by dividing the molecular weight of the desired product by the sum of the all substances produced in the stochiometric equation, i.e. if we consider the acylation of the anisole and veratrole by acetic anhydride by using clay, reactions are represented as under.

-continued

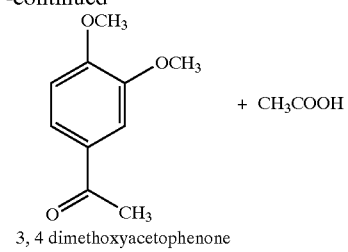

3, 4 dimethoxyacetophenone

Therefore in this reaction atom utilization is 151/210=71% for the acylation of anisole and 180/240=75% for the acylation of veratrole. E-factor is defined by the mass ratio of waste to desired product. In this reaction E-factor will be 60/151=0.4 for the acylation for anisole and 60/80=0.33 for the acylation of veratrole.

3. Catalyst being solid in nature can be easily separated the reaction mixture by filtration or centrifuge. Clay can be regenerated up to second cycle and re-used.

4 Shape selectivity towards para selectivity is observed in very high yield values for the products, 5 Clay based catalysts are easy in handling in comparison conventional Friedel-Craft acylation catalysts like $H_2SO_4$, HF, $AlCl_3$ and other Lewis acid.

6 Process uses inexpensive clay as a starting material for catalyst preparation.

We claim:

1. A process for the preparation of an acylated aromatic ether which comprises acylating the aromatic ether with an acylating agent in the presence of a solid acid heterogeneous catalyst comprising a rare earth cation exchanged clay based catalyst, the process being carried out at an ether to catalyst ratio in the range of 1:5, separating the catalyst and the acylated aromatic ether obtained.

2. A process as claimed in claim 1 wherein the lanthanide cation exchanged clay catalyst is an upgraded smectite clay wherein the hydrogen ion is exchanged with a sodium ion.

3. A process as claimed in claim 2 wherein the hydrogen ion is exchanged with a sodium ion using an acid selected from the group consisting of HCl, $HNO_3$, and an organic acid.

4. A process as claimed in claim 1 wherein the rare earth ion is selected from the group consisting of lanthanum, cerium, neodymium, praseodymium and samarium.

5. A process as claimed in claim 4 wherein the amount of rare earth ion in the catalyst is in the range of 5 to 10 weight % of the clay.

6. A process as claimed in claim 4 wherein the rare earth ion is obtained using a soluble salt of the rare earth selected from the group consisting of nitrate, chloride and acetate.

7. A process as claimed in claim 1 wherein the acylation of the aromatic ether is carried out in a single step under solvent free condition and at a temperature in the range of 80 to 120° C. and under atmospheric conditions without generating any by-product.

8. A process as claimed in claim 7 wherein the acylation of the aromatic ether is carried out at a temperature of 100° C.

9. A process as claimed in claim 1, wherein the acylating agent is selected from the group consisting of a chloride and a carboxylic acid anhydride.

10. A process as claimed in claim 8 wherein the carboxylic acid anhydride is acetic acid anhydride or a homologue thereof.

11. A process as claimed in claim 1 wherein the catalyst is separated and recycled.

12. A process as claimed in claim 1 wherein the aromatic ether is selected from the group consisting of veratrole and anisole.

13. A process as claimed in claim 1 wherein the process is solvent free with the aromatic ether itself acting as the solvent.

14. A process as claimed in claim 1 wherein the catalytic reaction is carried out at a pressure in the range from 1 to 20 atmospheres.

15. A process as claimed in claim 1 wherein the ether to catalyst ratio is in the range of 1:3 to 1:5.

16. A clay based catalytic process for the preparation of an acylated aromatic ether which comprises (i) preparing upgraded smectite clay in the range of 0.5 to 5% weight percent; (ii) drying the clay in the temperature of 80 to 120° C. for 8 to 12 hours; (iii)exchanging hydrogen ion for sodium ion using a mineral acid selected from the group consisting of HCl and $HNO_3$ or an organic acid; (iv) preparing Lanthanide exchanged clay using a soluble salt of a lanthanide cation; (v) maintaining the ether to catalyst ratio in the range of 1 to 5; mixing the catalyst so prepared with the aromatic ether and an acylating agent and acylating the aromatic ether at a reaction temperature in the range of 80 to 120° C. and time in the range of 1 to 9 hours under solvent free reaction mixture at atmospheric

\* \* \* \* \*